United States Patent
Cheng et al.

(10) Patent No.: US 7,045,357 B2
(45) Date of Patent: *May 16, 2006

(54) EFFICIENCY AGROBACTERIUM-MEDIATED PLANT TRANSFORMATION METHOD

(75) Inventors: Ming Cheng, Ballwin, MO (US); Joyce E. Fry, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/459,022

(22) Filed: Dec. 10, 1999

(65) Prior Publication Data

US 2001/0054186 A1    Dec. 20, 2001

Related U.S. Application Data

(60) Provisional application No. 60/111,795, filed on Dec. 11, 1998.

(51) Int. Cl.
| | |
|---|---|
| *C12N 15/82* | (2006.01) |
| *C12N 1/12* | (2006.01) |
| *C12N 5/10* | (2006.01) |
| *A01H 11/00* | (2006.01) |
| *C07H 21/04* | (2006.01) |

(52) U.S. Cl. ............... 435/469; 435/252.2; 435/320.1; 435/419; 435/424; 435/426; 435/430; 435/430.1; 800/278; 800/294; 800/298; 800/295; 536/23.1; 536/24.1

(58) Field of Classification Search ........... 800/320, 800/321.1, 295, 278, 294, 298; 536/24.1, 536/23.1; 435/469, 252.5, 320.1, 419, 430, 435/424, 426, 431, 252.2
See application file for complete search history.

(56) References Cited

U.S. PATENT DOCUMENTS 5,668,292 A * 9/1997 Somerville et al.

FOREIGN PATENT DOCUMENTS

| EP | 0 672 752 | 9/1994 |
|---|---|---|
| WO | WO 94 02620 | 7/1993 |

OTHER PUBLICATIONS

Hei et al. Efficient Transformation of Rice (*Oryza sativa* L.) Mediated by *Agrobacterium*. . . The Plant Journal (1994) 6(2), 271-282.*
Di et al. Prod. of Transgenic Soybean Lines Expressing . . . Plant Cell Reports. (1996) 15:746-750.*
Biochemistry & Molecular Biology of Plants, Buchanan et al, eds, 2000, American Society of Plant Physiologists, Rockville, MD, p. 1158 and p. 1162).*
Chee, P, et al, in *Agrobacterium* Protocols, K. Gartland and M Davey, eds, (1995) Humana Press, Totowa, NJ, pp. 101-119.*
Webster's Dictionary, 1994, p. 900.*
Hua, et al., Plant Physiology (Rockville), (1989) vol. 89, No. 4 SUPPL, pp. 188, Jul. 30-Aug. 3, 1989.*
Tanford, Physical Biochemistry of Macromolecules, p. 183, Wiley Publishers, 1961.*
P.J. Dale, "Agroinfection of wheat: inoculation of in vitro grown seedlings and embryos," Plant Science, 10th ed., Elsevier Scientific Publishers Ireland Ltd., p. 237-45, (Jul. 27, 1989).
M. Uze et al, "Plasmolysis of precultured inmmature embryos improves Agrobacterium mediated gene transfer to rice (*Oryza sativa* L.)," Plant Science, Elsevier Scientific Publishers Ireland Ltd., p. 87-95, (Jul. 27, 1997).
Zhanyuan Zhang et al, "Factors affecting *Agrobacterium*-mediated transformation of common bean," J. Amer. Soc. Hort. Sci., vol. 122 (No. 3), p. 300-05.

* cited by examiner

*Primary Examiner*—Phuong T. Bui
*Assistant Examiner*—Georgia Helmer
(74) *Attorney, Agent, or Firm*—M. Todd Rands

(57) ABSTRACT

The present invention relates to a rapid transformation and regeneration system for plants. In particular, the invention relates to a plant tissue preparation system. The transformation method is efficient and reliable for production of fertile plants with improved agronomic qualities.

8 Claims, 3 Drawing Sheets

EFFICIENCY AGROBACTERIUM-MEDIATED PLANT TRANSFORMATION METHOD

This application claims the benefit of Provisional application Ser. No. 60/111,795, filed Dec. 11, 1998.

BACKGROUND OF THE INVENTION

The present invention relates to the field of plant biotechnology. More specifically, it concerns methods of incorporating genetic components into the genome of monocotyledonous or dicotyledonous plants. In particular, provided herein are reproducible systems for genetically transforming corn, soybean, rice and wheat. Most particularly, there is a system for transforming wheat.

The method comprises novel conditions during co-culture of Agrobacterium with a regenerable plant cell or tissue. Exemplary methods include an improved method using Agrobacterium-mediated transformation for introducing nucleic acids into different regenerable tissues using a variety of selectable or screenable marker systems, and with a number of different plant species. The present invention also provides fertile transgenic plants, particularly wheat. In other aspects, the invention relates to the production of stable transformed and fertile plants, gametes, and offspring from these plants.

During the past decade, it has become possible to transfer genes from a wide range of organisms to crop plants by recombinant DNA technology. This advance has provided enormous opportunities to improve plant resistance to pests, disease and herbicides, and to modify biosynthetic processes to change the quality of plant products (Knutson et al., 1992; Piorer et al., 1992; Vasil et al., 1992). However, the availability of efficient Agrobacterium-mediated transformation methods suitable for high capacity production of economically important plants is limited.

There have been many methods attempted for plant transformation, but only a few methods are highly efficient. Methods for DNA transformation of plant cells include Agrobacterium-mediated plant transformation (see, for example, U.S. Pat. Nos. 5,416,011 and 5,569,834 and WO 97/48814). In addition, protoplast transformation, gene transfer into pollen, injection into reproductive organs, injection into immature embryos, and particle bombardment have been employed for plant transformation. Despite the number of transformation methods available for specific plant systems, it would be advantageous to have one method of introducing genes into plants that is applicable to several different crops and a variety of regenerable tissues.

Several technologies for the introduction of DNA into cells are well known to those of skill in the art and can be divided into categories including: (1) chemical methods (Graham and van der Eb, 1973; Zatloukal et al., 1992); (2) physical methods such as microinjection (Capecchi, 1980), electroporation (Wong and Neuman, 1982; Fromm et al., 1985; U.S. Pat. No. 5,384,253), and the gene gun (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992);

Until recently, the methods employed for some monocot species included direct DNA transfer into isolated protoplasts and microprojectile-mediated DNA delivery (Shimamoto et al., 1989; Fromm et al, 1990). The protoplast methods have been widely used in rice, where DNA is delivered to the protoplasts through liposomes, PEG, and electroporation. While a large number of transgenic plants have been recovered in several laboratories (Shimamoto et al., 1989; Datta et al., 1990), the protoplast methods require the establishment of long-term embryogenic suspension cultures. Some regenerants from protoplasts are infertile and phenotypically abnormal due to the long-term suspension culture (Davey et al., 1991; Rhodes et al.,1988). U.S. Pat. No. 5,631,152 describes a rapid and efficient microprojectile bombardment method for the transformation and regeneration of monocots and dicots.

More recently, monocot species have been successfully transformed via Agrobacterium-mediated transformation. WO 97/48814 discloses processes for producing stably transformed fertile wheat. The method describes the recovery of transgenic, wheat plants within a short period of time using a variety of explants. Agrobacterium-mediated transformation provides a viable alternative to bombardment methods, and the method also allows quick molecular analysis of transgenic lines.

The major deficiencies in current plant transformation systems utilizing Agrobacterium-mediated methods include the production efficiency of the system and transformation difficulties due to genotype or species diversity and explant limitations. WO 94/00977 describes a method for transforming monocots that depends on the use of freshly cultured immature embryos for one monocot and cultured immature embryos or callus for a different monocot. In either system, the explants must be freshly isolated, and the method is labor intensive, genotype-, and explant-limited. Other reports rely on the use of specific strains or vectors to achieve high efficiency transformation. In one report, a specific super binary vector must be used in order to achieve high-efficiency transformation (Ishida et al., 1996).

Despite the number of transformation methods in the art, few methods have been developed that are applicable to both monocots and dicots. The present invention provides an improvement of an Agrobacterium-mediated transformation method. The method is more efficient in delivering target DNA to the plant as evidenced by higher transformation efficiencies and provides a reduction in labor and cost advantage compared with conventional methods.

SUMMARY OF THE INVENTION

The present invention provides a method for producing a fertile transgenic plant the genome of which has been modified through the introduction of one or more genetic components, comprising the steps of:

(a) introducing a genetic component comprising a DNA composition one desires to introduce into the genome of said plant;

(b) co-culturing a regenerable cell or tissue with Agrobacterium under conditions that decrease the weight of the explant;

(c) identifying or selecting a transformed cell line; and (d) regenerating a fertile transgenic plant therefrom.

DETAILED DESCRIPTION OF THE INVENTION

Figure 1:
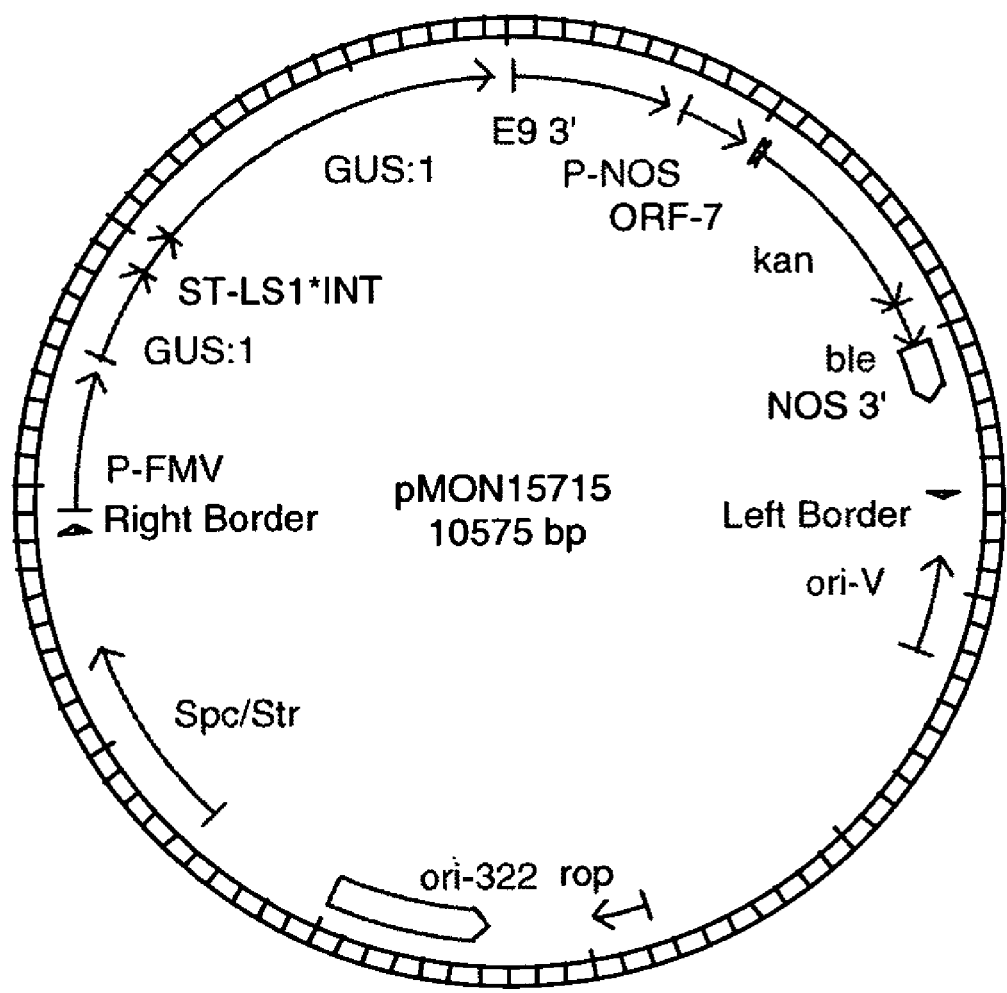
FIG. 1 is a representation of pMON15715.

The present invention can be used with any plant species. It is particularly useful for monocot species. Particularly preferred species for practice of the present invention include wheat, corn, rice, and soybean.

The present invention provides a fertile transgenic plant and a method for transformation of plant cells or tissues and regeneration of the transformed cells or tissues into a differentiated transformed plant. To initiate a transformation process in accordance with the present invention, it is first necessary to select genetic components to be inserted into the plant cells or tissues. Genetic components can include any nucleic acid that is introduced into a plant cell or tissue using the method according to the invention. Genetic components can include non-plant DNA, plant DNA, or synthetic DNA.

In a preferred embodiment, the genetic components are incorporated into a DNA composition such as a recombinant, double-stranded plasmid or vector molecule comprising at least one or more of the following types of genetic components:
 (a) a promoter that functions in plant cells to cause the production of an RNA sequence,
 (b) a structural DNA sequence that causes the production of an RNA sequence that encodes a product of agronomic utility,
 (c) a 3' non-translated DNA sequence that functions in plant cells to cause the addition of polyadenylated nucleotides to the 3' end of the RNA sequence.

The vector may contain a number of genetic components to facilitate transformation of the plant cell or tissue and regulate expression of the desired gene(s).

In one preferred embodiment, the genetic components are oriented so as to express a mRNA, which in one embodiment can be translated into a protein. The expression of a plant structural coding sequence (a gene, cDNA, synthetic DNA, or other DNA) that exists in double-stranded form involves transcription of messenger RNA (mRNA) from one strand of the DNA by RNA polymerase enzyme and subsequent processing of the mRNA primary transcript inside the nucleus. This processing involves a 3' non-translated region that adds polyadenylated nucleotides to the 3' ends of the mRNA.

Means for preparing plasmids or vectors containing the desired genetic components are well known in the art. Vectors used to transform plants and methods of making those vectors are described in U.S. Pat. Nos. 4,971,908, 4,940,835, 4,769,061 and 4,757,011, the entirety of which are incorporated herein by reference. Vectors typically consist of a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control.

Transcription of DNA into mRNA is regulated by a region of DNA usually referred to as the "promoter." The promoter region contains a sequence of bases that signals RNA polymerase to associate with the DNA and to initiate the transcription into mRNA using one of the DNA strands as a template to make a corresponding complementary strand of RNA.

A number of promoters that are active in plant cells have been described in the literature. Such promoters would include, but are not limited to, the nopaline synthase (NOS) and octopine synthase (OCS) promoters, which are carried on tumor-inducing plasmids of *Agrobacterium tumefaciens*; the caulimovirus promoters such as the cauliflower mosaic virus (CaMV) 19S and 35S promoters and the figwort mosaic virus (FMV) 35S promoter; the enhanced CaMV35S promoter (e35S); and the light-inducible promoter from the small subunit of ribulose bisphosphate carboxylase (ssRUBISCO, a very abundant plant polypeptide). All of these promoters have been used to create various types of DNA constructs that have been expressed in plants. See, for example PCT publication WO 84/02913.

Promoter hybrids can also be constructed to enhance transcriptional activity (U.S. Pat. No. 5,106,739) or to combine desired transcriptional activity, inducibility, and tissue or developmental specificity. Promoters that function in plants are promoters that are inducible, viral, synthetic, constitutive as described (Poszkowski et al., 1989; Odell et al., 1985), and temporally regulated, spatially regulated, and spatio-temporally regulated (Chau et al., 1989). Other promoters that are tissue-enhanced, tissue-specific, or developmentally regulated are also known in the art and envisioned to have utility in the practice of this invention.

Promoters may be obtained from a variety of sources such as plants and plant DNA viruses and include, but are not limited to, the CaMV35S and FMV35S promoters and promoters isolated from plant genes such as ssRUBISCO genes. As described below, it is preferred that the particular promoter selected should be capable of causing sufficient expression to result in the production of an effective amount of the gene product of interest.

The promoters used in the DNA constructs (i.e., chimeric/recombinant plant genes) of the present invention may be modified, if desired, to affect their control characteristics. Promoters can be derived by means of ligation with operator regions, random or controlled mutagenesis, etc. Furthermore, the promoters may be altered to contain multiple "enhancer sequences" to assist in elevating gene expression. Examples of such enhancer sequences have been reported by Kay et al. (1987).

The mRNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. Such "enhancer" sequences may be desirable to increase or alter the translational efficiency of the resultant mRNA. The present invention is not limited to constructs wherein the non-translated region is derived from both the 5' non-translated sequence that accompanies the promoter sequence. Rather, the non-translated leader sequence can be derived from unrelated promoters or genes. (see, for example U.S. Pat. No. 5,362,865). Other genetic components that serve to enhance expression or affect transcription or translational of a gene are also envisioned as genetic components.

The 3' non-translated region of the chimeric constructs should contain a transcriptional terminator, or an element having equivalent function, and a polyadenylation signal, which functions in plants to cause the addition of polyadenylated nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 385,962, herein incorporated by reference in its entirety).

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' non-translated regions. RNA polymerase transcribes a coding DNA sequence through a site where polyadenylation occurs.

In one preferred embodiment, the vector contains a selectable, screenable, or scoreable marker gene. These genetic components are also referred to herein as functional genetic components, as they produce a product that serves a function in the identification of a transformed plant, or a product of desired utility. The DNA that serves as a selection device functions in a regenerable plant tissue to produce a compound that would confer upon the plant tissue resistance to an otherwise toxic compound. Genes of interest for use as a selectable, screenable, or scorable marker would include, but are not limited to, β-glucuronidase (GUS), green fluorescent protein (GFP), luciferase (LUX), antibiotic or herbicide tolerance genes. Examples of transposons and associated antibiotic resistance genes include the transposons Tns (bla), Tn5 (nptII), Tn7 (dhfr); penicillins; kanamycin (and neomycin, G418, bleomycin); methotrexate (and trimethoprim); chloramphenicol; and tetracycline.

Characteristics useful for selectable markers in plants have been outlined in a report on the use of microorganisms (Advisory Committee on Novel Foods and Processes, July 1994). These include:
  i) stringent selection with minimum number of nontransformed tissues;
  ii) large numbers of independent transformation events with no significant interference with the regeneration;
  iii) application to a large number of species; and
  iv) availability of an assay to score the tissues for presence of the marker.

As mentioned, several antibiotic resistance markers satisfy these criteria, including those resistant to kanamycin (nptII), hygromycin B (aph IV), and gentamycin (aac3 and aacC4).

A number of selectable marker genes are known in the art. Particularly preferred selectable marker genes for use in the present invention would include genes that confer resistance to compounds such as antibiotics like kanamycin (Dekeyser et al., 1989), and herbicides like glyphosate (Della-Cioppa et al., 1987). Other selection devices can also be implemented and would still fall within the scope of the present invention.

The present invention can be used with any suitable plant transformation plasmid or vector containing a selectable or screenable marker and associated regulatory elements as described, along with one or more nucleic acids expressed in a manner sufficient to confer a particular desirable trait. Examples of suitable structural genes of interest envisioned by the present invention would include, but are not limited to, genes for insect or pest tolerance, herbicide tolerance, genes for quality improvements such as yield, nutritional enhancements, environmental or stress tolerances, or any desirable changes in plant physiology, growth, development, morphology, or plant product(s).

Alternatively, the DNA coding sequences can affect these phenotypes by encoding a non-translatable RNA molecule that causes the targeted inhibition of expression of an endogenous gene, for example via antisense—or cosuppression-mediated mechanisms (see, for example, Bird et al., 1991). The RNA could also be a catalytic RNA molecule (i.e., a ribozyme) engineered to cleave a desired endogenous mRNA product (see, for example, Gibson and Shillitoe, 1997). Thus, any gene that produces a protein or mRNA that expresses a phenotype or morphology change of interest is useful for the practice of the present invention.

Exemplary nucleic acids that may be introduced by the methods encompassed by the present invention include, for example, DNA sequences or genes from another species, or even genes or sequences that originate with or are present in the same species but are incorporated into recipient cells by genetic engineering methods rather than classical reproduction or breeding techniques. However, the term exogenous is also intended to refer to genes that are not normally present in the cell being transformed or to genes that are not present in the form, structure, etc., as found in the transforming DNA segment or to genes that are normally present but a different expression is desirable. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

In light of this disclosure, numerous other possible selectable or screenable marker genes, regulatory elements, and other sequences of interest will be apparent to those of skill in the art. Therefore, the foregoing discussion is intended to be exemplary rather than exhaustive.

After the construction of the plant transformation vector or construct, said nucleic acid molecule, prepared as a DNA composition in vitro, is introduced into a suitable host such as *E. coli* and mated into another suitable host such as *Agrobacterium*, or directly transformed into competent *Agrobacteria*. These techniques are well-known to those of skill in the art and have been described for a number of plant systems including soybean, cotton, and wheat (see, for example, U.S. Pat. Nos. 5,569,834 and 5,159,135 and WO 97/48814 herein incorporated by reference in their entirety).

The present invention encompasses the use of bacterial strains to introduce one or more genetic components into plants. Those of skill in the art would recognize the utility of *Agrobacterium*-mediated transformation methods. Preferred strains would include, but are not limited to, *Agrobacterium tumefaciens* strain C58, a nopaline strain that is used to mediate the transfer of DNA into a plant cell; octopine strains, such as LBA4404; or agropine strains, e.g., EHA101, EHA105, or EHA109. The use of these strains for plant transformation has been reported, and the methods are familiar to those of skill in the art.

The present invention can be used with any regenerable cell or tissue. Those of skill in the art recognize that regenerable plant tissue generally refers to tissue that after insertion of exogenous DNA and appropriate culture conditions can form into a differentiated plant. Such tissue can include, but is not limited to, callus tissue, hypocotyl tissue, cotyledons, roots, and leaves. For example regenerable tissues can include calli or embryoids from anthers (Zhou and Konzak, 1989), microspores (Ziauddin et al., 1992), inflorescences (Barcelo et al., 1994), and leaf tissues (Conger et al., 1987). In wheat for example, immature embryos may be isolated from wheat spikelets. Other tissues are also envisioned to have utility in the practice of the present invention.

In one embodiment of the present invention, embryogenic callus tissue is used as the starting explant material. Embryogenic calli are produced from immature embryos. These calli can be produced by isolating and culturing immature embryos on a nutrient media containing carbohydrates and plant growth regulators.

Embryogenic callus or other target tissue for transformation of a particular crop may be isolated by a number of methods known to those of skill in the art. For example, WO 97/48814, incorporated herein by reference in its entirely, describes the isolation of wheat immature embryos and embryogenic callus. The isolation of wheat immature embryos is also described by Weeks et al. (1993) and Vasil et al. (1993).

Similarly, immature embryos of maize may be precultured on a suitable culture medium and used for *Agrobacterium* inoculation. In soybean, for example, suspension cell cultures can be developed from leaf tissue and maintained for an extended period before *Agrobacterium* inoculation. Hypocotyl sections are also envisioned as explants for soybean and can be prepared from germinated seedlings, as is known to those of skill in the art.

Another embodiment of the present invention is to use precultured cells or tissues as the starting material. Precultured, as used herein, means culturing the cells or tissues in an appropriate medium to support plant tissue growth prior to inoculation with *Agrobacterium*. The preculture of the regenerable cells or tissue prior to *Agrobacterium* inoculation can occur for an extended period of time, for example seven days or more. More preferably, the preculture period is for six days or less. Even more preferably, the preculture period is a shorter period of time such as about one hour to four days. Most preferably, the preculture period is from about one to three days. Examples of suitable media for preculture would include, but are not limited to, MS-based media (Murashige and Skoog, 1962) or N6-based media (Chu et al., 1978) supplemented with additional nutrients and/or plant growth regulators including, but not limited to, pichloram and 2,4-D (see Table 2). Those of skill in the art are familiar with the variety of tissue culture media that, when supplemented appropriately, support plant tissue growth and development. These tissue culture media can either be purchased as a commercial preparation or custom prepared and modified by those of skill in the art. Examples of such media would include, but are not limited to, Gamborg's media (Gamborg et al., 1968), McCown's Woody plant media (McCown and Loyd, 1981), Nitsch and Nitsch media (Nitsch and Nitsch, 1969), and Schenk and Hildebrandt media (Schenk and Hildebrandt, 1972) supplemented accordingly. Those of skill in the art are aware that media and media supplements such as nutrients and growth regulators for use in transformation and regeneration are usually optimized for the particular target crop of interest.

Once the regenerable plant tissue is isolated, the next step of the method is introducing the genetic components into the plant tissue. This process is also referred to herein as "transformation." The plant cells are transformed and each independently transformed plant cell is selected. The independent transformants are referred to as plant cell lines. A number of methods have been reported and can be used to insert genetic components into regenerable plant tissue.

Methods for transforming dicots, primarily by use of *Agrobacterium tumefaciens*, and obtaining transgenic plants have been published for a number of crops including cotton (U.S. Pat. No. 5,004,863; U.S. Pat. No. 5,159,135; U.S. Pat. No. 5,518,908; WO 97/43430), soybean (U.S. Pat. No. 5,569,834; U.S. Pat. No. 5,416,011; McCabe et al., 1988; Christou et al., 1988), *Brassica* (U.S. Pat. No. 5,463,174), and peanut (Cheng et al., 1996; De Kathen and Jacobsen, 1990).

Transformation of monocots using electroporation, particle bombardment, and *Agrobacterium* have also been reported. Transformation and plant regeneration have been achieved in asparagus (Bytebier et al., 1987), barley (Wan and Lemaux, 1994), maize (Rhodes et al., 1988; Ishida et al., 1996; Gordon-Kamm et al., 1990; Fromm et al., 1990; Koziel et al., 1993; Armstrong et al., 1995), oat (Somers et al., 1992), rice (Toriyama et al., 1988); Zhang and Wu, 1988; Zhang et al., 1988; Battraw and Hall, 1992; Christou et al., 1991; Park et al., 1996), sugarcane (Bower and Birch, 1992), tall fescue (Wang et al., 1992), and wheat (Vasil et al., 1992; Weeks et al., 1993).

The present invention utilizes *Agrobacterium*-mediated transformation. One advantage of the present invention is that regular binary vectors can used with the experiments in this invention. Transformation was achieved in all plant systems tested. The fact that a super binary vector may not be necessary provides added utility, because super binary vectors have been shown to be essential for achieving high transformation in another reported maize system (Ishida et al., 1996).

Regenerable tissue is inoculated with *Agrobacterium*, and the inoculated explant was treated such that the weight of the explant was reduced during the co-culture period. The treatment of regenerable cells or tissues after *Agrobacterium* inoculation comprises any method that reduces the weight of the inoculated explant and facilitates the DNA transfer process.

A particularly preferred embodiment of the invention uses limited or reduced moisture conditions to reduce explant weight after *Agrobacterium* inoculation. Possible methods to reduce the weight of the explant during co-culture could include, but are not limited to, restricting exogenous moisture to the explant during co-culture; reducing the weight of the explant by applying a vacuum during co-culture; increasing the osmotic potential of the media, for example, by use of mannitol, sorbitol, raffinose, or polyethylene glycol or combinations thereof; air drying the explant to reduce the weight of the explant by evaporation or applied air; or chemical means of extracting moisture from the explant during co-culture, for example, by placing the explant in a dessicating environment. Examples of suitable dessicants would include, but are not limited to, calcium oxide or sulfuric acid.

One preferred method of decreasing the weight of the *Agrobacterium*-inoculated explant is to limit the moisture supply to said explant during co-culture. Co-culture, as used herein, means the time from when the explant is inoculated with the *Agrobacterium* culture up to the time in which the *Agrobacterium* growth is suppressed by the addition of compounds or through processes that inhibit *Agrobacterium* growth. The *Agrobacterium*-inoculated explant is placed in a tissue culture vessel such as a petri plate that does not contain media containing a gelling agent. In one embodiment, the explant is placed on a suitable blotting material, including, but not limited to, filter paper that is placed in the petri plate.

The *Agrobacterium* strain harboring the plasmid or vector of interest is cultured on an appropriate culture medium, such as Luria Burtani (LB) supplemented with selective antibiotics for the strain and vector. Those of skill in the art are familiar with procedures for growth and suitable culture conditions for *Agrobacterium* as well as subsequent inoculation procedures. The density of the *Agrobacterium* culture used for inoculation and the ratio of *Agrobacterium* cells to explant can vary from one system to the next, and therefore optimization of these parameters for any transformation method is expected. Typically, an *Agrobacterium* culture is inoculated from a streaked plate or glycerol stock and is grown overnight and the bacterial cells are washed and resuspended in a culture medium suitable for inoculation of the explant. Suitable inoculation media for the present invention include, but are not limited to, 1/10 MS salts in CM4C media (Table 2) or a modified CM4C culture medium with a reduced salt concentration. In some cases, a surfactant including, but not limited to, Silwet (L77)(Wites, Hudson, Ohio) or pluronic F68 (Sigma, St. Louis, Mo.) may also be added to the inoculation medium at a low concentration. The explants are incubated with the washed and resuspended *Agrobacterium* cell suspension. The inoculation is generally performed at a temperature of about 20° C.–28° C., preferably about 23° C.–28° C. from about 1 minute to about 3 hours.

The amount of added liquid incubated with the explant during the co-culture period varies depending on the size of the culture vessel, the size/weight of the starting explants and the number of explants/plate. The amount of liquid added can range from 0 μL to 1000 μL, preferably 0 μL to 500 μL for a culture plate of 60×20 mm. The co-culture period can range from about one hour to about one week, preferably about one day to four days, more preferably about one day to three days. After the co-culture period, the weight of the *Agrobacterium*-inoculated explant is reduced by not more than about 50%. More preferably, the weight of the *Agrobacterium*-inoculated explant is reduced up to about 40%. Even more preferably, the weight of the *Agrobacterium*-inoculated explant is reduced up to about 30%.

After the co-culture period, the *Agrobacterium*-inoculated explants are cultured on an appropriate medium containing an agent to inhibit *Agrobacterium* growth. The *Agrobacterium*-inoculated explants are cultured on such a media generally from one to fourteen days, preferably from two to seven days. Those of skill in the art are aware of the appropriate media components to inhibit *Agrobacterium* growth. Such media components would include, but are not limited to, antibiotics such as carbenicillin or cefotaxime.

After the culture step to inhibit *Agrobacterium* growth, and preferably before the explants are placed on selective media, they are analyzed for efficiency of DNA delivery by a transient assay that detects the presence of a gene contained on the transformation vector, including, but not limited to, a screenable marker gene such as the gene that codes for β-glucuronidase (GUS). The total number of blue spots (indicating GUS expression) for a selected number of explants is used as a positive correlation of DNA transfer efficiency. Both the optimum amount of weight reduction during co-culture and transformation efficiency are predicted transiently and subsequently confirmed with high efficiency production of stable transformants.

In the preferred embodiment, after incubation on non-selective media containing the antibiotics to inhibit *Agrobacterium* growth without selective agents, the explants are cultured on selective growth media including, but not limited to, a callus-inducing media containing a selective agent. Typical selective agents include, but are not limited to, antibiotics such as geneticin (G418), paromomycin, or other chemicals such as glyphosate. The cultures are subsequently transferred to a regeneration media suitable for the production of transformed plantlets. Those of skill in the art are aware of the numerous types of media and transfer requirements that can be implemented and optimized for each plant system for plant transformation and regeneration. Consequently, such media and culture conditions disclosed in the present invention can be modified or substituted with nutritionally equivalent components, or similar processes for selection and regeneration, and still fall within the scope of the present invention.

The transformants produced are subsequently analyzed to determine the presence or absence of a particular nucleic acid of interest contained on the transformation vector. Molecular analyses can include, but are not limited to, Southern blots (Southern, 1975) or PCR (polymerase chain reaction) analyses. These and other well known methods can be performed to confirm the stability of the transformed plants produced by the methods disclosed. These methods are well known to those of skill in the art and have been reported (see, for example, Sambrook et al., 1989).

Those of skill in the art will appreciate the many advantages of the methods and compositions provided by the present invention. The following examples are included to demonstrate the preferred embodiments of the invention. It should be appreciated by those of skill in the art that the techniques disclosed in the examples represent techniques discovered by the inventors to function well in the practice of the invention and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Plasmid Vector Construction

Figure 2:
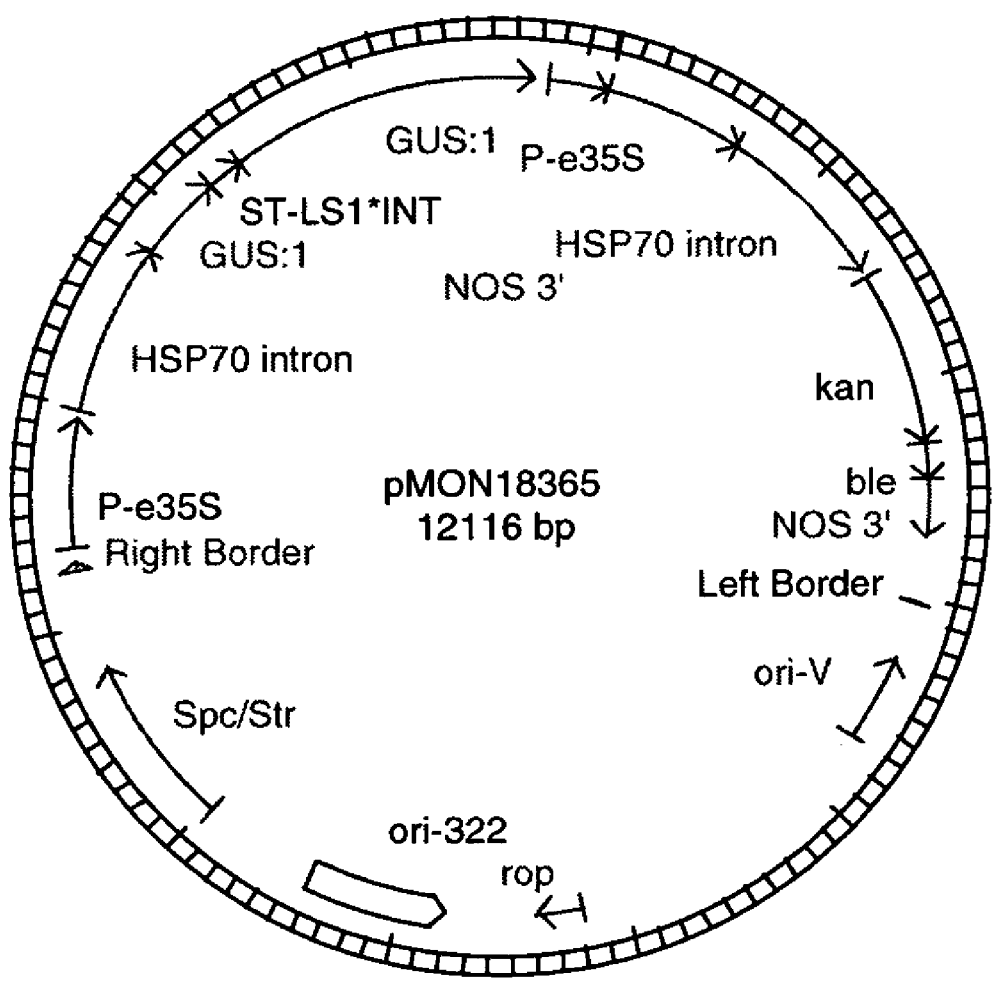
FIG. 2 is a representation of pMON18365.
Figure 3:
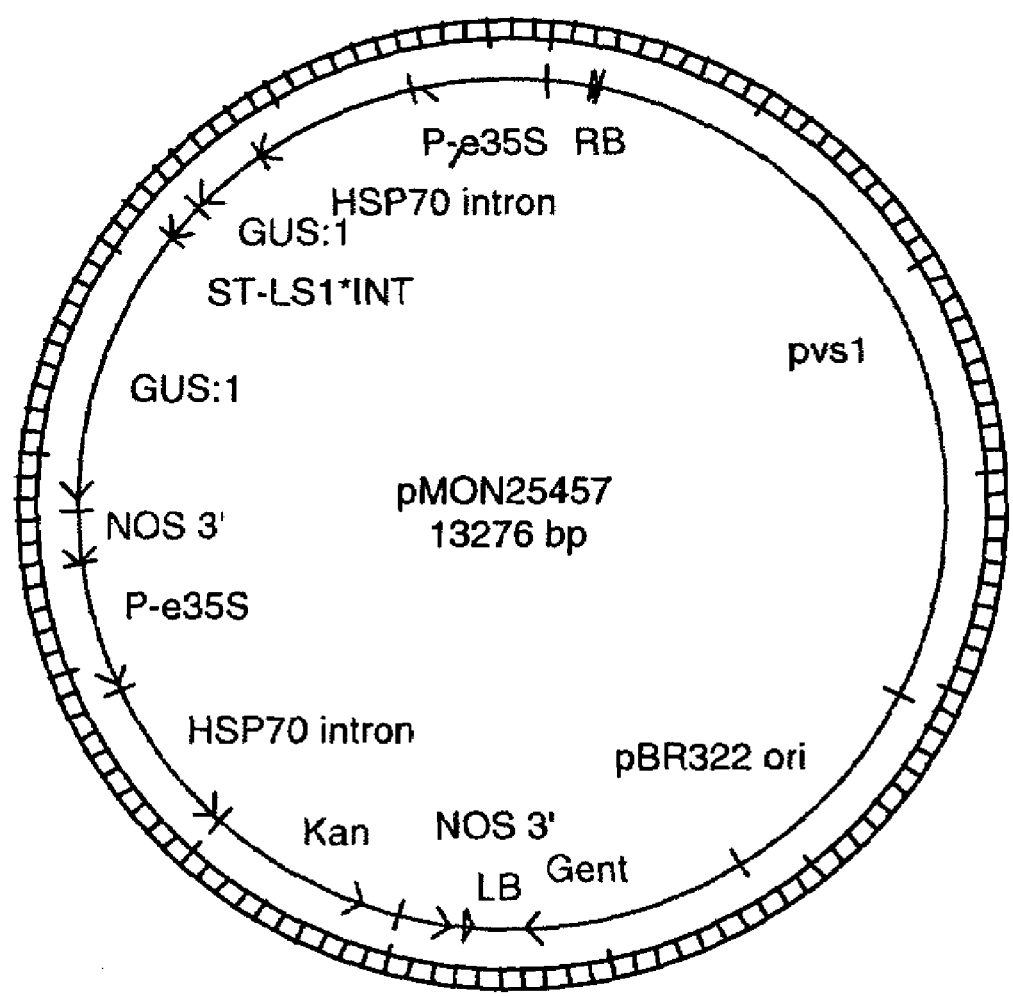
FIG. 3 is a representation of pMON25457.

Plasmid vectors were constructed using standard molecular biological techniques known to one of ordinary skill in the art. A number of *Agrobacterium*-mediated plant transformation vectors have been described (Klee and Rogers, 1989). Briefly, the plant transformation vectors described herein comprise one or more nucleic acid sequences including but not limited to one or more T-DNA border sequences to promote the transfer of nucleic acid molecules into the plant genome, replication elements, a selectable marker and one or more gene(s) of interest. pMON25457 (FIG. 3) also contains a maize heat shock protein (hsp70) intron located upstream from the coding region(s). pMON15715 (FIG. 1) and pMON18365 (FIG. 2) contain an intron from *Solanum tuberosum* (ST-LS 1 *INT). The basic features of the vectors used in the Examples are summarized in Table 1 and are listed as follows: promoter/coding sequence/3'-untranslated region.

The abbreviations in the table are described as follows: FMV is the promoter from the Figwort Mosaic Virus (U.S. Pat. No. 5,378,619); The e35S promoter is a modification of the 35S promoter derived from the 35S RNA of cauliflower mosaic virus (CaMV) which contains a duplication of the –90 to –300 region; The nos promoter is from *Agrobacterium tumefaciens* pTiT37. The GUS gene is the β-glucuronidase coding sequence form *E. coli*; The nptII gene codes for neomycin phosphotransferase; the nos 3' region contains downstream untranslated sequence and the poly A signal for the NOS gene of *Agrobacterium tumefaciens* pTiT37. Several glyphosate tolerance constructs were also tested using the CP4 gene as the gene of interest along with associated regulatory elements.

TABLE 1

Plasmid Vectors

| Plasmid | Genetic Elements |
|---|---|
| pMON15715 | pFMV-GUS-E93'/pnos-nptII-nos3' |
| pMON18365 | pe35S-nptII-nos3'/pe35S-GUS-nos3' |
| pMON25457 | pE35S-GUS-nos3'/pe35S-nptII-nos3" |

Example 2

Transformation Using Precultured Immature Embryos (PCIEs) of Wheat

1. Explant Preparation

Immature embryos of wheat (*Triticum aestivum* L) cv Bobwhite were isolated from the immature caryopsis (wheat spikelets) 13–15 days after pollination, and cultured on CM4C (Table 2) for 1–6 days. The embryos without embryogenic callus were selected for *Agrobacterium* inoculation.

TABLE 2

Supplemental Components in Basal Media[1]

| Components | CM4 | CM4C | MMS.2C | MMS0 |
|---|---|---|---|---|
| 2,4-D (mg/L) |  | 0.5 | 0.5 | 0.2 |
| Picloram (mg/L)[2] | 2.2 | 2.2 |  |  |
| Maltose (g/L) | 40.0 | 40.0 | 40.0 | 40.0 |
| Glutamine (g/L) | 0.5 | 0.5 |  |  |
| Magnesium Chloride (g/L) | 0.75 | 0.7 |  |  |
| Casein Hydrolysate (g/L) | 0.1 | 0.1 |  |  |
| MES (g/L) |  | 1.95 | 1.95 | 1.95 |
| Ascorbic Acid (mg/L)[2] |  | 100.0 | 100.0 | 100.0 |
| Gelling Agent (g/L)[3] | 2(P) | 2(P) | 2(G) | 2(G) |

[1]All media contain basal salts (MS basal salts) and vitamins (MS vitamins) from Murashige and Skoog (1962). The pH in each medium was adjusted to 5.8.
[2]Filter-sterilized and added to the medium after autoclaving.
[3]PHYTAGEL (P) (PHYTAGEL is a registered trademark of Sigma Chemical Co., St. Louis, MO) or GELRITE (G) (GELRITE is available from Schweizerhall, Inc., South Plainfield NJ) (GELRITE is a registered trademark of Monsanto Company, St. Louis, MO).

2. *Agrobacterium* Culture and Inoculation

A disarmed *Agrobacterium* strain C58 (ABI) harboring a binary vector was used for all the experiments. Cultures of *Agrobacterium* were initiated from glycerol stocks or from a freshly streaked plate and grown overnight at 26° C.–28° C. with shaking (approximately 150 rpm) to mid-log phase (about $OD_{660}$=1–1.5) in liquid LB medium, pH 7.0 (Miller, 1972) containing 50 mg/L kanamycin, 50 mg/L streptomycin and spectinomycin, and 25 mg/L chloramphenicol with 200 μM acetosyringone (AS). The *Agrobacterium* cells were resuspended in the inoculation medium and the density was adjusted to an $OD_{660}$ of 1. The immature embryos cultured in CM4C medium were transferred into sterile petri plates (16×20 mm) or wells of a 6-well cell culture plate (Costar Corporation, Cambridge, Mass.) containing 10 mL of inoculation medium per petri plate or 5 mL per cell culture cluster plate. An equal amount of the *Agrobacterium* cell suspension was added such that the final concentration of *Agrobacterium* cells was an $OD_{600}$ of 0.5. In most experiments, pluronic F68 was added to the inoculation mixture at a final concentration of 0.01%. The ratio between the *Agrobacterium* and immature embryos (IEs) was about 10 mL: 20–200 IEs. The conditions for inoculation were temperatures from about 23° C.–26° C. with a duration from about 5–60 minutes.

3. Co-culture

After the inoculation period, the remaining *Agrobacterium* cells were removed from the explants by using the in-house vacuum equipment. A piece of sterile Whatman No. 1 filter paper (to fit the size of the petri plate) was placed in each of 60×15 or 60×20 mm petri dishes without additional liquid or agar-supplemented media. Two hundred microliters of sterile water was placed in the middle of the filter paper. After 2–3 minutes, the inoculated immature embryos were placed in the plates. Usually, 20–50 explants are grouped as one stack (about 1 in size and 60–80 mg/stack), with 4–5 stacks on each plate. The plates were immediately parafilmed and then co-cultivated in the dark at 24° C.–26° C. for 2–3 days.

4. Effect of Moisture during Co-Culture on DNA Delivery, *Agrobacterium* Growth and Explant Weight The efficiency of DNA delivery was measured by transient GUS expression after a 2–3—day delay of selection. The effect of the moisture during co-culture on the DNA delivery was tested using the precultured explants. As shown in Table 3, when 300 μL or less of water was added to the co-culture plates, the weight of the explants was reduced by about 20%–35%. Significantly more transient GUS expression was also observed. When 400 μL or more of water was added, the weight of the explants was increased and fewer GUS spots were observed on the explants. The transient GUS expression was significantly reduced when a short time of inoculation (5–30 minutes) was used coupled with 500 μL or more of water in the co-culture plates. When 300 μL or less of water was used for the co-culture, the blue spots, indicative of GUS expression, were uniformly dispersed on the surface of the scutellar tissue of all the immature embryos, especially in the area showing active cell division. In constrast, only 30%–50% of the immature embryos showed GUS expression when 500 μL or more of water was added during co-culture.

TABLE 3

Effect of Moisture During Co-Culture on the Growth of *Agrobacterium*, the Weight of the inoculated PCIE, and the DNA delivery[1]

| $H_2O$/plate (μL) | Weight before Co-Culture[2] (grams) (A) | Weight after Co-Culture (grams) (B) | Gain+/loss− (C = B − A) (grams) | % (gain/loss) (C/A) × 100 | No. of Agro colonies[3] | No. of GUS spots/ IE[4] |
|---|---|---|---|---|---|---|
| 0 | 0.24351 | 0.15864 | −0.08487 | −34.8 | 251 | 105 |
| 100 | 0.27871 | 0.21456 | −0.06415 | −23.0 | 274 | 208 |
| 200 | 0.32957 | 0.25648 | −0.07309 | −22.2 | 279 | 219 |
| 300 | 0.35865 | 0.28576 | −0.07289 | −20.3 | 372 | 213 |

TABLE 3-continued

Effect of Moisture During Co-Culture on the Growth of
Agrobacterium, the Weight of the inoculated PCIE, and
the DNA delivery[1]

| $H_2O$/plate (μL) | Weight before Co-Culture[2] (grams) (A) | Weight after Co-Culture (grams) (B) | Gain+/loss− (C = B − A) (grams) | % (gain/loss) (C/A) × 100 | No. of Agro colonies[3] | No. of GUS spots/ IE[4] |
|---|---|---|---|---|---|---|
| 400 | 0.21412 | 0.22171 | +0.00759 | +3.5 | 672 | 93 |
| 500 | 0.33199 | 0.39501 | +0.06302 | +19.0 | 842 | 84 |

[1]pMON18365 was used.
[2]Each plate (treatment) contained 100 PCIEs.
[3]Ninety-five inoculated PCIEs after 3-day co-culture with *Agrobacterium* were rinsed with 10 mL of $H_2O$ supplemented with 0.01% L77 for 5 min, then 100 μL was taken and diluted to 10 mL of $H_2O$. One microliter from treatment 400 and 500 ($H_2O$/plate) and 10 μL from the remaining treatments were plated onto LB plus appropriate drugs, and the plates were incubated at 28° C. for 3 days. The individual colonies were counted, and the number was adjusted based on 10 μL diluted solution.
[4]Five explants were analyzed by a GUS assay and the blue spots were counted.

5. Selection and Regeneration

After 2–3 days on the delay medium, the immature embryos were transferred to CM4C supplemented with 25 mg/L G418 and 500 mg/L carbenicillin. After 2–3 weeks, the embryos were broken into smaller pieces (~2 mm) and subcultured to the first regeneration medium, MMS.2C (Table 2) with 25 mg/L G418 and 250 mg/L carbenicillin. Upon transfer to the regeneration medium, each piece of callus was further divided into several small pieces (~2 mm). Two weeks post-transfer, young shoots and viable callus tissue were transferred to a second generation medium MMS0C (Table 2) with the same concentrations of G418 and cabernicillin. Larger pieces of tissues were separated into smaller pieces as previously described. Plantlets, which were confirmed later to be true transformants, grew vigorously and formed strong root systems on this medium. The plants with strong root hairs, with more than ten short and strong roots, or secondary roots, were transferred to Sundae cups (Sweetheart Cup Company, Chicago, Ill.) containing the second regeneration medium for further growth and selection. Leaf samples were taken from some of the plantlets for the GUS histochemical assay at this time. During the growth period in the Sundae cups, most of the non-transformants died or showed signs of susceptibility to G418. The plants highly resistant to G418, which grew vigorously with strong root systems, were transferred to soil before they grew to the top of the Sundae cups. All the plants that originated from the same embryo were considered to be siblings from the same event.

6. Transformation Efficiency

The regenerated plants showed no visible abnormalities and were fertile. All the plants were tested by a GUS histochemical assay. Many transgenic events were produced. For a total of 1519 explants from 12 separate experiments, 99 transgenic events were produced, with an average transformation efficiency of 6.5%. The range in transformation efficiency was from 1.4% to 19% for the different parameters tested, which included duration of inoculation period and the *Agrobacterium* density used for inoculation.

7. Detection and Analysis of the Transgenic Plants

The plants were grown in an environmentally controlled growth chamber with a 16 hour photoperiod at 800 molm$^{-2}$ s$^{-1}$ provided by high-intensity discharge (HID) Sylvania lights (GTE Products Corp., Manchester, N.H.). The day/night temperatures were 18/16° C. It took about 2.5 to 3 months from inoculation to transferring most of the plants to soil, and no visible abnormalities were observed. Each plant was examined by one or more of the following methods:
 1) GUS histochemical calorimetric assay (Jefferson, 1987) using different parts of the plants.
 2) A leaf bleach assay as described in Cheng et al. (1997).
 3) Southern hybridization analysis (Southern, 1975) is also conducted. Genomic DNA is isolated from leaf tissue of test plants using standard methods known to those of skill in the art (see, for example the method described in Roger and Bendich,1985). Once the DNA is isolated, Southern analyses can be performed using protocols and methods that are known to those of skill in the art.

Example 3

Transformation of Embryogenic Callus of Wheat Using NptII Selection

1. Explant Preparation

A spring wheat *Triticum aestivum* cv. Bobwhite was used throughout this study. The stock plants were grown in an environmentally controlled growth chamber under the same growth conditions as described previously. Immature caryopses (spikelets) were collected from the plants 13–15 days after anthesis. Immature embryos (IEs) were dissected aseptically and cultured on CM4 or CM4C callus induction medium (Table 2) for 10–30 days at 23–25° C. in the dark.

2. *Agrobacterium* Culture

The protocol for *Agrobacterium* culture and harvest was the same as described in Example 2, and pMON18365 was used.

3. Inoculation

The immature embryos cultured in the callus induction medium (CM4 or CM4C) for 10–30 days were transferred into an *Agrobacterium* cell suspension in petri dishes (25× 100 mm). The ratio between *Agrobacterium* and embryogenic callus tissue (EC) was about 30 mL *Agrobacterium*: 30 EC. A surfactant, Silwet (L77) (Witco Corporation, Hudson, Ohio) or pluronic F68 (Sigma, St. Louis, Mo.), was added to the inoculation medium at a concentration of 0.01–0.02%. The inoculation was performed at 23° C.–25° C. for 2–3 hours in the dark.

4. Co-Cultivation

After inoculation, the extra *Agrobacteria* in liquid culture were removed from the explants by using the in-house vacuum equipment. A piece of sterile Whatman No. 1 filter paper was placed in each of 60×20 mm petri dishes. Fifty microliters of inoculation medium or sterile water was placed in the middle of the filter paper. After one to two minutes, the inoculated embryogenic calli (derived from each immature embryo cultured for 10–30 days) were placed at the ridge of the liquid medium or water. Usually, about 10–12 explants were placed in a circle on the filter paper of each plate. The plates were parafilmed and the co-cultivation allowed to proceed in the dark at 24° C. to 25° C. for three days.

5. Efficiency of DNA Delivery

The efficiency of DNA delivery was measured by a transient GUS expression assay after a 2–3 day delay of selection. A higher level of GUS expression was observed for all the experiments that limited moisture to the *Agrobacterium*-inoculated explant. As shown in Table 4, when 200 μL or less liquid medium was added to the co-culture plates, significantly more transient GUS expression was observed. When 400 μL or more medium was added, less than 40 GUS spots were visible on the explants.

TABLE 4

Effect of Moisture During Co-Culture on DNA Delivery Using 14-day Cultured Immature Embryos[1]

| Amount of liquid added to the plate (μL) | Number of blue spots/explant[2] |
| --- | --- |
| 500 | 33.9 |
| 400 | 27.6 |
| 300 | 46.1 |
| 200 | 89.4 |
| 100 | 83.4 |
| 50 | 139.3 |
| 0 | 70.6 |

[1]pMON18365 was used.
[2]Ten explants were assayed in this experiment

6. Selection and Plant Regeneration

After 2–5 days on the CM4C medium (Table 2), the *Agrobacterium*-inoculated embryogenic calli were transferred to CM4 or CM4C (Table 2) containing 25 mg/L G418 and 500 mg/L carbenicillen. Each embryogenic callus was separated into 5 or 6 pieces, and each piece was treated as a single explant. The embryogenic calli were cultured for 2–3 weeks for callus induction before transfer to the first regeneration media and subsequent culture methods are as outlined in Example 2.

7. Detection and Analysis of the Transgenic Plants.

The $T_1$ plants were analyzed as described in Example 2.

8. Transformation Efficiency

The number of transgenic events in each experiment were determined after the plants were assayed as described. From 10 separate experiments, 53 positive transgenic events were obtained from a total of 515 initial explants. The transformation efficiency ranged from 3.6% to 37.7%, with an average of 10%. Treatment parameters included the surfactant type and the concentration and amount of water in the plate during the co-culture period.

9. Progeny Analysis of the Transgenic Plants

The segregation of the GUS and NPTII genes in the $T_1$ progeny was analyzed by either a GUS histochemical assay on the leaf tissue, or a paromomycin spray test on the $T_1$ seedlings. The $T_1$ seeds harvested from each $T_0$ plant were planted in 2" pots grown under the same conditions as the stock plants described earlier. Plants at the three-leaf stage were sprayed with 2% (w/v) paromomycin containing 0.2% Tween 20 (both available from Sigma Chemical Co., St. Louis, Mo.). One week later, the plants were evaluated for paromomycin sensitivity. The plants with a functional NPTII gene were not bleached, while plants without a functional NPTII gene exhibited bleached spots. The data were then analyzed by $\chi^2$ test to determine the number of functional GUS or NPTII gene loci (Table 5). For example, if the ratio of resistant to sensitive plants is 3:1, a single functional nptII gene loci is present in this transgenic event. If the ratio is greater than 3:1, more than one functional event is present.

TABLE 5

Segregation of the NPTII and GUS genes in the $T_1$ progeny of transgenic wheat[1]

| | $T_1$ Plant Assayed by Paromomycin Spray | | | $T_1$ Plants Assayed for GUS Activity | | |
| --- | --- | --- | --- | --- | --- | --- |
| Events | Resistance (R) | Sensitive (S) | R/S | Positive (+) | Negative (−) | +/− |
| 19733 | 24 | 11 | 3:1 | 24 | 11 | 3:1 |
| 19347 | 32 | 4 | 3:1 | 32 | 4 | 3:1 |
| 19745 | 14 | 17 | 1:1 | 14 | 17 | 1:1 |
| 19751 | 21 | 11 | 2:1 | 21 | 11 | 2:1 |
| 19748 | 14 | 17 | 1:1 | 14 | 17 | 1:1 |
| 19752 | 28 | 6 | 3:1 | 28 | 6 | 3:1 |
| 19357 | 32 | 0 | 32:0 | 32 | 0 | 32:0 |
| 19741 | 11 | 23 | 1:2 | 11 | 23 | 1:2 |
| 19354 | 33 | 1 | 15:1 | 33 | 1 | 15:1 |
| 19735 | 32 | 0 | 32:0 | 32 | 0 | 32:0 |

[1]All Lines Derived from Construct pMON18365

Example 4

Transformation of Wheat Using Glyphosate Selection

1. Explant Preparation

The procedures for the growth of stock plants, isolation of immature embryos, and induction culture were the same as described in Example 2. The explants were either 3–6 day precultured immature embryos (PCIE) without embryogenic callus tissue, or 10–30 day cultured embryogenic callus tissue.

2. *Agrobacterium* Preparation, Inoculation, Co-Cultivation and T-DNA Delivery

The protocols were the same as described in Examples 2 and 3.

3. Selection and Plant Regeneration

After a 3-day co-cultivation, the *Agrobacterium*-infected PCIE and embryogenic calli were transferred to CM4C medium (Table 2) supplemented with 500 mg/L carbenicillin and cultured for about seven days. The PCIE explants formed embryogenic callus on this medium. The explants were then transferred to CM4C selection medium with 2 mM glyphosate and 500 mg/L carbenicillin for one week in the dark. All the calli were transferred to MMS0.2C (Table 2) supplemented with 0.1 mM glyphosate and 250 mg/L carbenicillin for an additional two weeks of selection with lighting conditions of about 80 μE. Green spots or shoots formed at the end of this culture period. All the embryogenic calli were transferred to the second regeneration medium MMS0C (Table 2) supplemented with 500 mg/L carbenicillin and 0.02 mM glyphosate. Aromatic amino acids including L-tryptophan and L-phenylalanine ($10^{-7}$ mM/amino acid) were added to this medium to facilitate the selection. These tissues were transferred to fresh media every two weeks. Plantlets with elongated meristems and roots could be regenerated from embryogenic callus tissue any time during the culture period. Once the root system was established, the plants were transferred to soil and subsequently assayed. All the plants originating from the same PCIE or callus were considered as siblings from the same transgenic event.

4. Confirmation of the Transgenic Nature of the Plants

Transgenic plants survived the glyphosate selection and were grown in the growth chamber with the same environmental conditions as described in Example 2. Transgenic plants were usually examined either by glyphosate selection (all plants surviving glyphosate selection were considered to be transformants) or Southern hybridization (Southern, 1975).

5. Transformation Efficiency

Glyphosate-tolerant transgenic plants were also produced using the *Agrobacterium* transformation method of the present invention. Both 10–14—day—old callus tissue and 3–6—day precultured immature embryos were used as explants. All putative transgenic plants were confirmed to be positive by the assay methods described. The average transformation efficiency from 12 experiments was 4.6% (a total of 2844 explants resulted in 131 transgenic events). The range in transformation efficiency was from 3.3% to 6.7%.

6. Progeny Analysis of the Transgenic Plants

The segregation of CP4 and GUS genes in the $T_1$ generation was tested either by a GUS histochemical assay on leaf tissue and root tissue or a Roundup® spray test of 64–128 ounces per acre at the 3–6 leaf stage. The data were analyzed by a $\chi^2$ test to determine the number of functional CP4 and GUS gene loci. Twenty-one lines were analyzed (17 CP4, 4 GUS). Of the CP4 lines, progeny of 11 lines exhibited a 3:1 segregation ratio (resistant: sensitive), 5 lines exhibited a 15:1 ratio and 1 line a 1:1 ratio. Of the GUS lines, progeny of 4 lines exhibited a 3:1 ratio (positive: negative), 2 lines exhibited a 1:1 ratio and 1 line a 15:1 ratio. Over 500 total progeny were analyzed.

Example 5

Transformation of Embryogenic Calli of Maize

1. Explant Preparation

Immature embryos of maize (*Zea mays* L.) three-way cross (Pa91×H99)×A188 and inbred line H99 (1 to 1.5 mm in length), were cultured in Medium D (Duncan et al., 1985) supplemented with 1.5 mg/l 2,4-D (MediumD-1.5D) for 14 days at 27° C. in the dark.

2. *Agrobacterium* Preparation, Inoculation and Co-Culture

Disarmed *Agrobacterium* strain EHA101 (Hood et al., 1986) harboring vector pMON25457 was used for the maize transformation. Cultures of *Agrobacterium* were initiated, grown, and harvested as described in Example 2; however, the cells were selected with different antibiotics (100 mg/L gentamycin and kanamycin). The cell density was adjusted to an $OD_{660}$ of 0.5 to 1.0 for inoculation. Embryogenic calli (14 day, precultured) were soaked in the *Agrobacterium* suspension cells for 3 hours at 23° C. to 25° C. in the dark. Usually, 0.01% Silwet (L77) was included in the inoculation mixture. After inoculation, *Agrobacterium* cells were removed from the inoculation plates as described, and the explants were co-cultured as described in Examples 2 and 3. Usually 50–300 μL of water was added to each co-culture plate. Treatments with 500 μL or more of water added to the co-culture plates were used as controls.

3. Plant Regeneration and Identification of the Transgenic Plants

After 3 days on the delay medium (MediumD-1.5D with 500 mg/L carbenicillin), the *Agrobacterium*-infected precultured immature embryos or embryogenic calli were transferred to the modified Medium D as described, with 500 mg/L carbenicillin, and supplemented with paromomycin for a stepwise selection. The explants were selected with 25 mg/L paromomycin for one week, then broken down and subcultured to medium with paromomycin in concentrations of 50 mg/L, 100 mg/L and 200 mg/L at two or three-week intervals. The viable tissues were transferred to BA pulse medium, which consisted of Medium D supplemented with 0.5 mg/L benzyladenine (BA). After 5 days, the embryogenic calli were transferred to MS basal medium for plant regeneration. Transgenic plants were identified by a histochemical GUS assay. Table 6 shows the effects of moisture-deprivation during co-culture on GUS expression.

TABLE 6

DNA Delivery and Transformation Efficiency

| Treatments[1] | Medium for Induction of Embryogenic Callus | Moisture Conditions (μL/plate[3]) | Transient GUS Expression | No. Events/ Total Explants |
|---|---|---|---|---|
| 1 | CM4C | 1,000 | few | 0/15 |
| 2 | MediumD-1.5D | 1,000 | few | 0/16 |
| 3 | Peanut P[4] | 1,000 | few | 1/7 |
| 4 | MediumD-1.5D | 1,000 | few | 0/20 |
| 5 | CM4C | 200 | many | 0/5 |
| 6 | MediumD-1.5D | 200 | many | 2/19 |
| 7 | Peanut P | 200 | many | 0/24 |
| 8 | MediumD-1.5D | 200 | moderate | 0/20 |

[1]Treatment 1–3, 5–7 using genotype (Pa91 × H99)A188; treatment 4 and 8 using genotype H99
[2]Immature embryos of (Pa91 × H99)A188 cultured on various media for 14 days prior to inoculation. Embryogenic calli of H99 were initiated and maintained on MediumD-1.5D medium for over 2 months prior to inoculation.
[3]Petri plates 60 × 20 mm were used for co-culture; one piece of filter paper in center of plate
[4]Peanut P medium consisted of MS basal medium plus vitamins supplemented with 3 mg/L picloram and solidified with GELRITE.

Example 6

Transformation of Cells in Suspension and Precultured Hypocotyledonary Explants of Soybean 1. Explant Preparation A suspension cell culture was initiated from callus induced from leaf tissue of soybean cv. A3237 on MS basal medium supplemented with 1 mg/L 2,4-D and 0.1 mg/L benzyladenine (BA). The suspension cells were maintained on this medium for two months before inoculation. The cells were harvested from the liquid culture and inoculated with *Agrobacterium*. Hypocotyl sections were prepared from five-day-old germinated seedlings of cv. A3237. The hypocotyls were cut into about 0.5 cm sections. The explants were precultured on various media for 5 days before inoculation.

2. *Agrobacterium* Preparation, Inoculation and Co-Culture

Disarmed *Agrobacterium* strain ABI harboring binary vector pMON15715 was used for all the soybean experiments. Cultures of *Agrobacterium* were initiated, grown and harvested as described previously. The cell density was adjusted to an $OD_{660}$ of 0.1 to 1.0 for inoculation. The explants were soaked in the *Agrobacterium* solution for 15 to 30 minutes, and the infected explants were co-cultured in petri plates (100×20 mm, 100×15 mm, or 60×20 mm) with one piece of filter paper in the petri plate. Water or liquid medium was excluded during the co-culture period to test the effect of moisture, and controls were set up using 500 μL or 1000 μL water or liquid medium during co-culture. The co-culture was performed at 23° C.–25° C. for 3 days in the dark.

3. Efficiency of DNA Delivery

After 2 days delay of selection on a modified MS medium (designated Peanut P) with 500 mg/L carbenicillin, the explants were analyzed by a GUS assay. Significantly more transient GUS expression (~50-fold) was shown in the moisture limitation treatment using suspension cells compared with the controls. A positive effect of limiting moisture to the *Agrobacterium*-inoculated explants on DNA delivery was also observed on the hypocotyl explants. The effect was more pronounced under different preculture media conditions as shown in Table 7.

TABLE 7

Effect of Moisture and Preculture Media on DNA Delivery to Soybean Hypocotyl Explants[1]

| Media for Preculture | Transient GUS Expression Under Moisture Deprivation Conditions |
|---|---|
| CM4C | ~10-fold enhancement over control |
| Peanut P[2] | ~100-fold enhancement |
| Peanut TDZ[3] | same as control |
| MediumD-1.5D | ~10-fold |

[1]No water during co-culture
[2]Peanut P = MS-based media plus vitamins plus 3 mg/L picloram
[3]Peanut TDZ medium consisted of MS basal salts plus vitamins supplemented with 2 mg/L TDZ; (TDZ = thidiazuran, Sigma, St. Louis, MO).

REFERENCES

The references listed below and all references cited herein are incorporated herein by reference to the extent that they supplement, explain, provide a background for, or teach methodology, techniques, and/or compositions employed herein.

Armstrong et al., *Crop Science*, 35:550–557, 1995.
Barcelo et al., *Plant J.*, 5:583–592, 1994.
Battraw and Hall, *Plant Sci.* 86(2):191–202, 1992.
Bird et al., *Biotech Gen. Engin. Rev.*, 9:207–227, 1991.
Bower and Birch, *Plant J.*, 2:409–416, 1992.
Bytebier et al., *Proc. Natl. Acad. Sci. USA* 84:5345, 1987.
Capecchi, *Cell*, 22(2):479–488, 1980.
Chau et al., *Science*, 244:174–181, 1989.
Cheng et al., *Plant Cell Rep.*, 15(9):653–657, 1996.
Cheng et al., *Plant Physiol.*, 115(3): 971–980, 1997.
Christou et al., *Plant Physiol.*, 87:671–674, 1988.
Christou et al., *Bio/Technology* 9:957, 1991.
Chu, *Proc. Symp. Plant Tissue Culture*. Peking: Science Press. Pp.43–50, 1978.
Clapp, *Clin. Perinatol.*, 20(1):155–168, 1993.
Conger et al., *Plant Cell Rep.*, 6:345–347, 1987.
Curiel et al., *Hum. Gen. Ther.*, 3(2):147–154, 1992.
Datta et al., *Bio/Technology*, 8:736–740, 1990.
Davey et al., *J. Exp. Bot.*, 42:1129–1169, 1991.
De Kathen and Jacobsen, *Plant Cell Rep.*, 9(5):276–279, 1990.
Dekeyser et al., *Plant Physiol.*, 90:217–223, 1989.
Della-Cioppa et al., *Bio/Technology*, 5:579–584, 1987.
Duncan et al., *Planta*, 165:322–332, 1985.
Eglitis and Anderson, *Biotechniques*, 6(7):608–614, 1988.
Fromm et al., *Proc. Natl. Acad. Sci. USA*, 82(17):5824–5828, 1985.
Fromm et al., *Bio/Technology*, 8:833–839, 1990.
Fynan et al, *Proc. Natl. Acad. Sci. USA*, 90(24):11478–11482, 1993.
Gamborg et al., *Exp. Cell Res.*, 50:151, 1968.
Gibson and Shillitoe, *Mol. Biotech.*, 7:125–137, 1997.
Gordon-Kamm et al., *Plant Cell*, 2:603–618, 1990.
Graham and van der Eb, *Virology*, 54(2):536–539, 1973.
Hood et al., *J. Bacteriol.*, 168:1291–1301, 1986.
Ishida et al., *Nature Biotech.*, 745–750, 1996.
Jefferson, *Plant Mol. Biol. Rep.*, 5:387–405, 1987.
Johnston and Tang, *Methods in Cell Biology*, 43:353–365, 1994.
Kay et al., *Science*, 236:1299, 1987.
Klee and Rogers, *Cell Culture and Somatic Cell Genetics of Plants*. Academic Press. 6:1–23, 1989.
Knutson et al., *Proc. Natl. Acad. Sci. USA*, 89:2624–2628, 1992.
Koziel et al., *Bio/Technology*, 11:194, 1993.
Lu et al., *J. Exp. Med.*, 178(6):2089–2096, 1993.
McCabe et al., *Bio/Technology*, 6:923, 1988.
McCown and Lloyd, *HortScience*, 16:453, 1981.
Miller, Cold Spring Harbor Laboratory Press, Cold Spring Harbor, N.Y., 1972.
Murashige and Skoog, *Physiol. Plant*, 15:473–497, 1962.
Nitsch and Nitsch, *Science*, 163:85–87, 1969.
Odell et al., *Nature*, 313:810, 1985.
Parketal., *Plant Mol. Biol.* 32(6):1135–1148, 1996.
Piorer et al., *Science*, 256:520–523, 1992.
Poszkowski et al, *EMBO J.*, 3:2719, 1989.
Rhodes et al., *Science*, 240:204, 1988.
Roger and Bendich, *Plant Mol. Biol.*, 5:69–76, 1985.
Sambrook et al., *Molecular Cloning: A Laboratory Manual*, Second Edition, Cold Spring Harbor Laboratory Press, Cold Spring Harbor, N.Y., 1989.
Schenk and Hildebrandt, *Can. J. Bot.* 50:199–204, 1972.
Shimamoto et al., *Nature*, 338:274–276, 1989.
Somers et al., *Bio/Technology* 10:1589, 1992.
Southern, *Mol. Biol.*, 98:503–517, 1975.
Toriyama et al., *BioTechnology.* 6:1072–1074, 1988.
Vasil et al., *Bio/Technology*, 10:667–674, 1992.
Vasil et al., *Bio/Technology*, 11:1153–1158, 1993.
Wagner et al., *Proc. Natl. Acad. Sci. USA*, 89(13):6099–6103, 1992.
Wan and Lemaux, *Plant Physiol.* 104:37, 1994.
Wang et al., *Bio/Technology* 10:691, 1992.
Weeks et al., *Plant Physiol*, 102:1077–1084, 1993.
Wong and Neuman, *Biochim. Biophys. Res. Commun.*, 107 (2):584–587, 1982.
Zatloukal et al., *Ann. N.Y. Acad. Sci.*, 660:136–153, 1992.
Zhang and Wu, *Theor. Appl. Genet.* 76:835, 1988.
Zhang et al., *Plant Cell Rep.*, 7:379, 1988.
Zhou and Konzak, Crop Sci, 29:817–821, 1989.
Ziauddin et al., *Plant Cell Rep.*, 11:489–493, 1992.

The invention claimed is:

1. A method for producing a fertile transgenic plant, comprising the steps of:
 (a) inoculating a regenerable plant cell or tissue selected from the group consisting of wheat immature embryos, maize immature embryos, wheat embryogenic callus, maize embryogenic callus, soybean hypocotyl sections and soybean callus suspension cell cultures with a solution comprising *Agrobacterium* containing a genetic component, said genetic component comprising a nucleic acid sequence of interest encoding a selectable or screenable marker that functions in the identification of a transformed plant cell or tissue, to produce an *Agrobacterium*-inoculated explant;

(b) substantially removing said solution of *Agrobacterium*;
(c) co-culturing said *Agrobacterium*-inoculated explant in a vessel with about 100 to about 300 microliters of media, said media not containing a gelling agent wherein the weight of the *Agrobacterium*-inoculated explant is reduced from about 20% to about 35% by the end of the co-culture period;
(d) identifying and selecting a transformed plant cell or tissue comprising said genetic component; and
(e) regenerating a transgenic plant therefrom.

2. The method of claim 1 wherein the regenerable cell or tissue is an immature embryo and is precultured prior to step (a).

3. The method of claim 1 wherein the co-culture period is from one hour to about 6 days.

4. The method of claim 1 wherein the co-culture period is from about one day to about 4 days.

5. The method of claim 1 wherein the co-culture period is from about one day to about 3 days.

6. A method for producing a fertile transgenic plant, comprising the steps of:
(a) inoculating a regenerable plant cell or tissue selected from the group consisting of wheat immature embryos, maize immature embryos, wheat embryogenic callus, maize embryogenic callus, soybean hypocotyl sections and soybean callus cell suspension cell cultures with a solution comprising *Agrobacterium* containing a genetic component, said genetic component comprising a nucleic acid sequence of interest encoding a selectable or screenable marker that functions in the identification of a transformed plant cell or tissue, to produce an *Agrobacterium*-inoculated explant;
(b) substantially removing said solution of *Agrobacterium*;
(c) co-culturing said *Agrobacterium*-inoculated explant in a vessel with about 100 to about 300 microliters of media, said media not containing a gelling agent, wherein the weight of the *Agrobacterium*-inoculated explant is reduced from about 20% to about 35% by the end of the co-culture period and wherein the manner for controlling said reduction in the weight of the *Agrobacterium*-inoculated explant comprises limitation or removal of water from the vessel containing said explant;
(d) identifying and selecting a transformed plant cell or tissue comprising said genetic component; and
(e) regenerating a transgenic plant therefrom.

7. The method of claim 1 wherein the vessel contains filter paper.

8. The method of claim 6 wherein the vessel contains filter paper.

* * * * *